(12) United States Patent
Park et al.

(10) Patent No.: US 11,511,137 B2
(45) Date of Patent: Nov. 29, 2022

(54) ULTRASOUND DEVICE FOR FACILITATING WASTE CLEARANCE OF THE BRAIN LYMPHATIC SYSTEM

(71) Applicant: DEEPSONBIO CO., LTD., Seongnam-si (KR)

(72) Inventors: Woong Park, Seoul (KR); Gujin Chung, Seongnam-si (KR); Seungschik Yoo, Seoul (KR)

(73) Assignee: DEEPSONBIO CO., LTD., Seongnam-si (KR)

( * ) Notice: Subject to any disclaimer, the term of this patent is extended or adjusted under 35 U.S.C. 154(b) by 21 days.

(21) Appl. No.: 16/930,643

(22) Filed: Jul. 16, 2020

(65) Prior Publication Data
US 2022/0016444 A1 Jan. 20, 2022

(51) Int. Cl.
*A61N 7/00* (2006.01)

(52) U.S. Cl.
CPC ........ *A61N 7/00* (2013.01); *A61N 2007/0021* (2013.01); *A61N 2007/0039* (2013.01); *A61N 2007/0047* (2013.01); *A61N 2007/0078* (2013.01)

(58) Field of Classification Search
CPC .............. A61N 7/00; A61N 2007/0021; A61N 2007/0039; A61N 2007/0078; A61N 2007/0047
See application file for complete search history.

(56) References Cited

U.S. PATENT DOCUMENTS

| | | | |
|---|---|---|---|
| 5,636,179 A * | 6/1997 | Slomka | G01N 29/348 367/95 |
| 7,896,821 B1 | 3/2011 | Magnin et al. | |
| 10,525,277 B1 * | 1/2020 | Chau | A61N 1/325 |
| 2011/0178441 A1 * | 7/2011 | Tyler | C12N 5/0619 601/2 |
| 2015/0238772 A1 * | 8/2015 | Meyer | A61N 7/00 601/2 |

FOREIGN PATENT DOCUMENTS

| JP | 2018537147 A | 12/2018 |
|---|---|---|
| KR | 101143645 B1 | 5/2012 |
| KR | 10-2020-0049241 A | 5/2020 |

OTHER PUBLICATIONS

Britta Engelhardt et al., "The movers and shapers in immune privilege of the CNS", Nat Immunol, 2017. 18(2): p. 123-131.
(Continued)

*Primary Examiner* — Hien N Nguyen
(74) *Attorney, Agent, or Firm* — Novick, Kim & Lee PLLC; Jae Youn Kim

(57) ABSTRACT

An ultrasound device for facilitating waste clearance of the brain lymphatic system includes: a first frequency-generator generating a predetermined frequency; a first waveform modulator modulating a waveform of the frequency; a first linear amplifier amplifying the waveform; a first resonance circuit portion matching impedance of the amplified waveform; and a first ultrasound transducer coupled to the first resonance circuit portion and irradiating ultrasound toward the area of the brain of mammals, wherein the ultrasound facilitates clearance of lymphatic wastes of the brain.

7 Claims, 10 Drawing Sheets

(56) References Cited

OTHER PUBLICATIONS

Meyer et al., "Endothelial cells and lymphatics at the interface between the immune and central nervous systems", Implications for multiple sclerosis. Curr Opin Neurol, 2017. 30(3): p. 222-230.
Natale et al., "Scholars and scientists in the history of the lymphatic system", J Anat, 2017. 231(3): p. 417-429.
Ahn et al., "Meningeal lymphatic vessels at the skull base drain cerebrospinal fluid", Nature, 2019. 572(7767): p. 52-66.
Abbott et al., "The role of brain barriers in fluid movement in the CNS: is there a 'glymphatic' system?", Acta Neuropathol, 2018. 135(3): p. 387-407.
Jessen et al., "The Glymphatic System: A Beginner's Guide", Neurochem Res, 2015. 40(12): p. 2583-99.
Abbott et al., "Transporting therapeutics across the blood-brain barrier", Mol Med Today, 1996. 2(3): p. 106-13.
Cammalleri et al., "Therapeutic Potentials of Localized Blood-Brain Barrier Disruption by Noninvasive Transcranial Focused Ultrasound: A Technical Review", J Clin Neurophysiol, 2020. 37(2): p. 104-117.
Muoio et al., "The neurovascular unit—concept review", Acta Physiol (Oxf), 2014. 210(4): p. 790-8.
Li et al., "Aquaporin 1 and the Na(+)/K(+)/2Cl(-) cotransporter 1 are present in the leptomeningeal vasculature of the adult rodent central nervous system", Fluids Barriers CNS, 2020. 17(1): p. 15.
Iliff et al., "A paravascular pathway facilitates CSF flow through the brain parenchyma and the clearance of interstitial solutes, including amyloid beta", Sci Transl Med, 2012. 4(147): p. 147ra111.
Benveniste et al., "The Glymphatic System and Waste Clearance with Brain Aging: A Review", Gerontology, 2019. 65(2): p. 106-119.
Aspelund et al., "A dural lymphatic vascular system that drains brain interstitial fluid and macromolecules", J Exp Med, 2015. 212(7): p. 991-9.
Louveau et al., "Structural and functional features of central nervous system lymphatic vessels", Nature, 2015. 523 (7560): p. 337-41.
Da Mesquita et al., "Functional aspects of meningeal lymphatics in ageing and Alzheimer's disease.", Nature, 2018. 560(7717): p. 185-191.
Da Mesquita et al., "The Meningeal Lymphatic System: A New Player in Neurophysiology", Neuron, 2018. 100(2): p. 375-388.
Kress et al., "Impairment of paravascular clearance pathways in the aging brain", Ann Neurol, 2014. 76(6): p. 845-61.
Cserr et al., "Bulk flow of interstitial fluid after intracranial injection of blue dextran 2000", Exp Neurol, 1974.4 5(1): p. 50-60.
Cesrr et al., "Flow of cerebral interstitial fluid as indicated by the removal of extracellular markers from rat caudate nucleus", Exp Eye Res, 1977. 25 Suppl: p. 461-73.
Iliff et al., "Cerebral arterial pulsation drives paravascular CSF-interstitial fluid exchange in the murine brain", J Neurosci, 2013. 33(46): p. 18190-9.
Ilife et al., "Brain-wide pathway for waste clearance captured by contrast-enhanced MRI", J Clin Invest, 2013. 123(3): p. 1299-309.
Fultz et al., "Coupled electrophysiological, hemodynamic, and cerebrospinal fluid oscillations in human sleep", Science, 2019. 366(6465): p. 628-631.
Yamada et al., "Influence of respiration on cerebrospinal fluid movement using magnetic resonance spin labeling", Fluids Barriers CNS, 2013. 10(1): p. 36.
Xie et al., "Sleep drives metabolite clearance from the adult brain", science, 2013. 342(6156): p. 373-377.
Benvensiste et al., "Anesthesia with Dexmedetomidine and Low-dose Isoflurane Increases Solute Transport via the Glymphatic Pathway in Rat Brain When Compared with High-dose Isoflurane", Anesthesiology, 2017. 127(6): p. 976-988.
Lundgaard et al., "Glymphatic clearance controls state-dependent changes in brain lactate concentration.", J Cereb Blood Flow Metab, 2017. 37(6): p. 2112-2124.
Gakuba et al., "General Anesthesia Inhibits the Activity of the "Glymphatic System"", Theranostics, 2018. 8(3): p. 710-722.
Lee et al., "The Effect of Body Posture on Brain Glymphatic Transport", J Neurosci, 2015. 35(31): p. 11034-44.
Von Holstein-Rathlou et al., "Voluntary running enhances glymphatic influx in awake behaving, young mice", Neurosci Lett, 2018. 662: p. 253-258.
Smith et al., "Muddying the water in brain edema?", Trends Neurosci, 2015. 38(6): p. 331-2.
Smith et al., "Test of the 'glymphatic' hypothesis demonstrates diffusive and aquaporin-4-independent solute transport in rodent brain parenchyma", Elife, 2017. 6.
Holter et al., "Interstitial solute transport in 3D reconstructed neuropil occurs by diffusion rather than bulk flow", Proceedings of the National Academy of Sciences, 2017. 114(37): p. 9894-9899.
Pizzo et al., "Intrathecal antibody distribution in the rat brain: surface diffusion, perivascular transport and osmotic enhancement of delivery", J Physiol, 2018. 596(3): p. 445-475.
Papadopoulos et al., "Extracellular space diffusion in central nervous system: anisotropic diffusion measured by elliptical surface photobleaching", Biophys J, 2005. 89(5): p. 3660-8.
Rosenberg et al., "Bulk flow of brain interstitial fluid under normal and hyperosmolar conditions", Am J Physiol, 1980 238(1): p. F42-9.
Kiviniemi et al., "Ultra-fast magnetic resonance encephalography of physiological brain activity - Glymphatic pulsation mechanisms?", J Cereb Blood Flow Metab, 2016. 36(6): p. 1033-45.
Eide et al., "Magnetic resonance imaging provides evidence of glymphatic drainage from human brain to cervical ymph nodes", Sci Rep, 2018. 8(1): p. 7194.
Ringstad et al., "Brain-wide glymphatic enhancement and clearance in humans assessed with MRI", JCI Insight, 2018. 3(13).
Meng et al., "Glymphatics Visualization after Focused Ultrasound-Induced Blood-Brain Barrier Opening in Humans", Ann Neurol, 2019. 86(6): p. 975-980.
Wang et al., "Focal Solute Trapping and Global Glymphatic Pathway Impairment in a Murine Model of Multiple Microinfarcts", J Neurosci, 2017. 37(11): p. 2870-2877.
Pu et al., "Persistent Malfunction of Glymphatic and Meningeal Lymphatic Drainage in a Mouse Model of Subarachnoid Hemorrhage", Exp Neurobiol, 2019. 28(1): p. 104-118.
Iliff et al., "Impairment of glymphatic pathway function promotes tau pathology after traumatic brain injury", J Neurosci, 2014. 34(49): p. 16180-93.
Rasmussen et al., "The glymphatic pathway in neurological disorders", The Lancet Neurology, 2018. 17(11): p. 1016-1024.
Holth et al., "The sleep-wake cycle regulates brain interstitial fluid tau in mice and CSF tau in humans", Science, 2019. 363(6429): p. 880-884.
Hersh et al., "Pulsed ultrasound expands the extracellular and perivascular spaces of the brain", Brain Research Jun. 28, 2016, pp. 1-19.

* cited by examiner

ULTRASOUND DEVICE FOR FACILITATING WASTE CLEARANCE OF THE BRAIN LYMPHATIC SYSTEM

BACKGROUND

Technical Field

The present disclosure is related to an ultrasound device, more particularly to an ultrasound device for facilitating waste clearance of the brain lymphatic system.

Related Art

The lymphatic system is referred to a general term for various organs composed of lymphatic tissue/vessels, and lymph nodes, etc. Clearance of wastes and conservation of interstitial solutes, while balancing osmotic pressure gradient across cells, play crucial roles in normal function and homeostasis of the biological tissue. The lymphatic system collects plasma from the blood stream, along with various molecules or proteins, and drains them into peripheral lymphatic vessels. Therefore, the lymphatic system serves as drainage of various metabolic wastes, including cell debris and foreign molecules such as bacteria and macromolecules. Also as an important part of the immune system that involves the spleen, the thymus, and the bone marrow, the lymphatic system mediates immune cell trafficking and activation for adaptive immune responses [reference documents 1, 2].

Since the discovery of the lymphatic system in the 17$^{th}$ century, research on the its functional and anatomical feature has been conducted extensively [reference document 3]. Compared to the lymphatic systems elsewhere in the body, the lymphatic network in the central nervous system (CNS) has unique morphological features, for example, different shape of lymphatic endothelial cells and absence of valve structures in the part of the meningeal lymphatic vessels [referenced document 4]. As compared to other organs, the CNS in human shows extraordinarily high metabolic rates whereas the brain cells are extremely sensitive and vulnerable to intra-/extra-cellular environment; therefore, the CNS requires efficient and rapid waste clearance [reference documents 5, 6].

The CNS of mammals including the brain and the spine is immersed in cerebrospinal fluid (CSF). Cerebral vasculature that supplies blood to the CNS includes the blood-brain-barrier (BBB). The BBB acts as a physical barrier separating the blood circulating in the vasculature and protects the brain parenchyma from other foreign/immunogenic substances, while it allows for passive diffusional transport of water, lipid-/water-soluble molecules as well as facilitating active transport of key nutrients [referenced documents 7, 8]. Surrounding cerebral tissues including the BBB are referred to as Neurovascular Unit (NVU) and composed of cerebral vascular endothelial cells, pericytes, neurons, glial cells, smooth muscle cells and extracellular matrix components [reference document 9].

The CSF is mainly produced by the structure referred to as choroid plexus, in the ventricle. Recently, leptomeningeal vasculature itself was also found as the contributing site for CSF production [reference document 10]. The CSF moves to the arachnoid space, transported to the brain parenchyma through CSF/interstitial fluid (ISF) exchange, and eventually drained to perivenous space as well as to the lymphatic vessels via the olfactory bulb and cranial/spinal nerves [referenced documents 6, 11, 12]. Different classes of lymphatic vessels (e.g. the absence of lymphatic valves) were identified in the brain, typically being aligned along the blood vessels at the dural surface/meninges [reference documents 4, 13-15].

The interstitial space (ISS) between the neurons and glia in the brain parenchyma is occupied by the brain ISF, which has similar composition as the CSF. The ISF and CSF are believed to be continuously exchanged, hypothetically nearby the NVU [reference documents 5, 6, 9, 11, 16, 17], and perform an important role for clearing foreign materials and metabolic wastes into the lymphatic system. Despites decades of research, the extremely complicated outflow passages of materials in connection with osmotic/hydrostatic/hydrodynamic pressure are not clearly identified [reference documents 6, 12], thus requiring further investigation to delineate the exact mechanism of CSF/ISF exchange and drainage.

In the prior animal research conducted by Cserr et al. in 1970s, it was revealed that the CSF and ISF showed directional flow in the brain. They injected CSF tracers, having different molecular weight/sizes, directly into the caudate of the animal brain, and monitored its movement over time. Longer range transport of 40 kDa horseradish peroxidase (HRP), compared to the larger (2000 kDa) blue dextran suggested a presence of movement of these solutes through the interstitial space (ISS) [reference document 18, 19].

The question on how the exchange and drainage between CSF and ISF occur was rekindled by the research conducted by Nedergaard et al. using modern imaging techniques (in vitro 2 photon microscopy and high-resolution Magnetic Resonance Imaging (MRI)) [reference documents 11, 20]. Iliff affiliated with the same laboratory as Nedergaard injected fluorescence-labeled dextran and ovalbumin into the cistern of the brain of mice (i.e., CSF space), then monitored the movement thereof [reference document 11]. This research revealed the existence of the paravascular space, that are presumably mediated by the function of aquaporin-4 (AQP4) channels, which are expressed on the astroglial endfeet that surrounding the cerebral vasculature [reference documents 11, 21]. These research studies conjectured that that the CSF in the subarachnoid space flows to the perivascular Virchow-Robin space (VRS) that has low fluid resistance to CSF influx, and subsequently is transported to the brain parenchyma via AQP4 water channels, being facilitated by vascular pulsatility/motion and respiration [reference documents 20, 22, 23]. It was also conjectured that the net influx creates a convective bulk flow motion (hereinafter referred to as 'bulk flow') of the ISF toward peri-venous space, whereby ISF is collected in the cerebral lymphatic vessels and subsequently drained into the cervical lymph nodes [reference document 6].

Meanwhile, the clearance of metabolic byproducts existing in the brain ISF space, such as β-amyloid protein, tau protein and lactates, which were considered as being closely related to Alzheimer's disease (AD), was dependent on state of arousal [reference documents 24-27] or body posture (supine position or lateral decubitus position) [referenced 28]. Further, it was identified that physical activity was also a contributing factor in facilitating brain lymphatic influx in mice [reference document 29]. The clearance becomes inefficient with aging, along with phenotypic/morphological changes in cells consisting of meningeal lymphatics in mice [reference documents 15, 17].

It was shown that AQP4 channels help the flow of CSF into cerebral tissues, and perform a role for clearing solutes of β-amyloid in the brain through animal testing [reference documents 11, 17, 24]. Although the AQP4 were hypothesized as a source of bulk-flow (i.e. convective) movement of the solutes by 'propelling' the CSF into the ISF space, the exact role of AQP4 in ISF/CSF exchange is still debated [reference documents 5, 30, 31]. In more detail, according to the computer simulation and subsequent animal testing reproducing the solute movement in the brain [reference documents 5, 27, 30-33], CSF-ISF exchange occurs through diffusion, not bulk-flow, at least within the brain parenchyma (small molecules or compounds move via cerebral tissue interstitial fluid by osmotic pressure) while convective flow is more prominent along the perivascular spaces in the larger cerebral vessels through the pores on their surface (e.g., 'stomata' that lines leptomeningeal vessels and the pia) [reference document 5]. Meanwhile, it was observed that diffusion and bulk flow coexist in white matter tracts [reference document 35].

Researches based on animal testing have been extended to humans recently. Eide and Ringstad injected MRI contrast agents directly into the spinal cord of idiopathic normal pressure hydrocephalus (iNPH) patients or those with suspected CSF leaks, then studied CSF dynamics using magnetic resonance imaging (MRI) [reference documents 36]. This research showed that the MRI contrast agents injected in CSF spread out across the cerebral cortices, then were absorbed into the brain in maximum quantities after approximately 4-6 hours (differences exist depending on the brain regions), and were centripetally transported to deep brain areas along with the skull base direction in around 24 hours. Various arteries are distributed intensively in the skull base, and thus relatively many paravascular spaces exist therein as the final drainage stage [reference documents 37, 38]. This supports that the brain waste clearance may occur with the direction from the cerebral cortex to the deep brain area, particularly to the skull base in humans. Recently, temporary disruption of the BBB in humans, followed by injection of MRI contrast agents and its imaging, verified that the meningeal lymphatic system is present in humans [reference document 39].

Regarding the clinical manifestation of the abnormal brain lymphatic function, various small animal model studies have indicated that the aberrant brain lymphatic function may ramify into various neurological conditions. For example, impaired brain lymphatic function in AQP4 knock-out mice resulted in a significant reduction in clearance of radiolabeled (125I)-Aβ injected into the striatum, compared to that of the wild-type [reference document 11]. Impaired lymphatic function was also demonstrated in murine model of cerebral microinfarct and subarachnoid hemorrhage [reference documents 40, 41]. Particularly, Traumatic brain injury (TBI) in mice lead to decreased lymphatic influx and impaired clearance of intracortically-injected radiotracers from the brain for sustainable period (~1 month) while the injury increased accumulation of Tau proteins [reference document 42]. In Alzheimer's disease (AD) mouse model, age-dependent, less polar (i.e. more even) distribution of AQP4 expression in the brain parenchyma may indicate abnormal lymphatic function implicated in AD [reference documents 11, 43].

Apart from these relations to neurological conditions, the brain lymphatic clearance of the metabolite during sleep rose as another important area of investigation as the function of brain lymphatic system is closely associated with sleep [reference documents 24, 26]. Sleep deprivation and sleep-wake cycle influence the level of the Tau proteins in the ISF/CSF in both humans and mice [referenced document 44]. Based on these findings, it is plausible to conjecture that facilitated clearance of the waste products by enhancing the lymphatic function in the brain may compensate for suboptimal clearance of waste products, for example, accumulation of the lactate due to lack of sleep [reference document 26].

RELATED ART DOCUMENT

Non-Patent Document

1. Engelhardt, B., P. Vajkoczy, and R. O. Weller, The movers and shapers in immune privilege of the CNS. Nat Immunol, 2017. 18(2): p. 123-131.
2. Meyer, C., G. Martin-Blondel, and R. S. Liblau, Endothelial cells and lymphatics at the interface between the immune and central nervous systems: implications for multiple sclerosis. Curr Opin Neurol, 2017. 30(3): p. 222-230.
3. Natale, G., G. Bocci, and D. Ribatti, Scholars and scientists in the history of the lymphatic system. J Anat, 2017. 231(3): p. 417-429.
4. Ahn, J. H., et al., Meningeal lymphatic vessels at the skull base drain cerebrospinal fluid. Nature, 2019. 572(7767): p. 62-66.
5. Abbott, N. J., et al., The role of brain barriers in fluid movement in the CNS: is there a 'glymphatic' system? Acta Neuropathol, 2018. 135(3): p. 387-407.
6. Jessen, N. A., et al., The Glymphatic System: A Beginner's Guide. Neurochem Res, 2015. 40(12): p. 2583-99.
7. Abbott, N. J. and I. A. Romero, Transporting therapeutics across the blood-brain barrier. Mol Med Today, 1996. 2(3): p. 106-13.
8. Cammalleri, A., et al., Therapeutic Potentials of Localized Blood-Brain Barrier Disruption by Noninvasive Transcranial Focused Ultrasound: A Technical Review. J Clin Neurophysiol, 2020. 37(2): p. 104-117.
9. Muoio, V., P. B. Persson, and M. M. Sendeski, The neurovascular unit—concept review. Acta Physiol (Oxf), 2014. 210(4): p. 790-8.
10. Li, Q., et al., Aquaporin 1 and the Na(+)/K(+)/2Cl(−) cotransporter 1 are present in the leptomeningeal vasculature of the adult rodent central nervous system. Fluids Barriers CNS, 2020. 17(1): p. 15.
11. Iliff, J. J., et al., A paravascular pathway facilitates CSF flow through the brain parenchyma and the clearance of interstitial solutes, including amyloid beta. Sci Transl Med, 2012. 4(147): p. 147ra111.
12. Benveniste, H., et al., The Glymphatic System and Waste Clearance with Brain Aging: A Review. Gerontology, 2019. 65(2): p. 106-119.
13. Aspelund, A., et al., A dural lymphatic vascular system that drains brain interstitial fluid and macromolecules. J Exp Med, 2015. 212(7): p. 991-9.
14. Louveau, A., et al., Structural and functional features of central nervous system lymphatic vessels. Nature, 2015. 523(7560): p. 337-41.
15. Da Mesquita, S., et al., Functional aspects of meningeal lymphatics in ageing and Alzheimer's disease. Nature, 2018. 560(7717): p. 185-191.
16. Da Mesquita, S., Z. Fu, and J. Kipnis, The Meningeal Lymphatic System: A New Player in Neurophysiology. Neuron, 2018. 100(2): p. 375-388.
17. Kress, B. T., et al., Impairment of paravascular clearance pathways in the aging brain. Ann Neurol, 2014. 76(6): p. 845-61.
18. Cserr, H. F. and L. H. Ostrach, Bulk flow of interstitial fluid after intracranial injection of blue dextran 2000. Exp Neurol, 1974. 45(1): p. 50-60.

19. Cserr, H. F., D. N. Cooper, and T. H. Milhorat, Flow of cerebral interstitial fluid as indicated by the removal of extracellular markers from rat caudate nucleus. Exp Eye Res, 1977. 25 Suppl: p. 461-73.
20. Iliff, J. J., et al., Cerebral arterial pulsation drives paravascular CSF-interstitial fluid exchange in the murine brain. J Neurosci, 2013. 33(46): p. 18190-9.
21. Iliff, J. J., et al., Brain-wide pathway for waste clearance captured by contrast-enhanced MRI. J Clin Invest, 2013. 123(3): p. 1299-309.
22. Fultz, N. E., et al., Coupled electrophysiological, hemodynamic, and cerebrospinal fluid oscillations in human sleep. Science, 2019. 366(6465): p. 628-631.
23. Yamada, S., et al., Influence of respiration on cerebrospinal fluid movement using magnetic resonance spin labeling. Fluids Barriers CNS, 2013. 10(1): p. 36.
24. Xie, L., et al., Sleep drives metabolite clearance from the adult brain. science, 2013. 342(6156): p. 373-377.
25. Benveniste, H., et al., Anesthesia with Dexmedetomidine and Low-dose Isoflurane Increases Solute Transport via the Glymphatic Pathway in Rat Brain When Compared with High-dose Isoflurane. Anesthesiology, 2017. 127(6): p. 976-988.
26. Lundgaard, I., et al., Glymphatic clearance controls state-dependent changes in brain lactate concentration. J Cereb Blood Flow Metab, 2017. 37(6): p. 2112-2124.
27. Gakuba, C., et al., General Anesthesia Inhibits the Activity of the "Glymphatic System". Theranostics, 2018. 8(3): p. 710-722.
28. Lee, H., et al., The Effect of Body Posture on Brain Glymphatic Transport. J Neurosci, 2015. 35(31): p. 11034-44.
29. von Holstein-Rathlou, S., N. C. Petersen, and M. Nedergaard, Voluntary running enhances glymphatic influx in awake behaving, young mice. Neurosci Lett, 2018. 662: p. 253-258.
30. Smith, A. J., B. J. Jin, and A. S. Verkman, Muddying the water in brain edema? Trends Neurosci, 2015. 38(6): p. 331-2.
31. Smith, A. J., et al., Test of the 'glymphatic' hypothesis demonstrates diffusive and aquaporin-4-independent solute transport in rodent brain parenchyma. Elife, 2017. 6.
32. Holter, K. E., et al., Interstitial solute transport in 3D reconstructed neuropil occurs by diffusion rather than bulk flow. Proceedings of the National Academy of Sciences, 2017. 114(37): p. 9894-9899.
33. Pizzo, M. E., et al., Intrathecal antibody distribution in the rat brain: surface diffusion, perivascular transport and osmotic enhancement of delivery. J Physiol, 2018. 596(3): p. 445-475.
34. Papadopoulos, M. C., J. K. Kim, and A. S. Verkman, Extracellular space diffusion in central nervous system: anisotropic diffusion measured by elliptical surface photobleaching. Biophys J, 2005. 89(5): p. 3660-8.
35. Rosenberg, G. A., W. T. Kyner, and E. Estrada, Bulk flow of brain interstitial fluid under normal and hyperosmolar conditions. Am J Physiol, 1980. 238(1): p. F42-9.
36. Kiviniemi, V., et al., Ultra-fast magnetic resonance encephalography of physiological brain activity—Glymphatic pulsation mechanisms? J Cereb Blood Flow Metab, 2016. 36(6): p. 1033-45.
37. Eide, P. K., et al., Magnetic resonance imaging provides evidence of glymphatic drainage from human brain to cervical lymph nodes. Sci Rep, 2018. 8(1): p. 7194.
38. Ringstad, G., et al., Brain-wide glymphatic enhancement and clearance in humans assessed with MRI. JCI Insight, 2018. 3(13).
39. Meng, Y., et al., Glymphatics Visualization after Focused Ultrasound-Induced Blood-Brain Barrier Opening in Humans. Ann Neurol, 2019. 86(6): p. 975-980.
40. Wang, M., et al., Focal Solute Trapping and Global Glymphatic Pathway Impairment in a Murine Model of Multiple Microinfarcts. J Neurosci, 2017. 37(11): p. 2870-2877.
41. Pu, T., et al., Persistent Malfunction of Glymphatic and Meningeal Lymphatic Drainage in a Mouse Model of Subarachnoid Hemorrhage. Exp Neurobiol, 2019. 28(1): p. 104-118.
42. Iliff, J. J., et al., Impairment of glymphatic pathway function promotes tau pathology after traumatic brain injury. J Neurosci, 2014. 34(49): p. 16180-93.
43. Rasmussen, M. K., H. Mestre, and M. Nedergaard, The glymphatic pathway in neurological disorders. The Lancet Neurology, 2018. 17(11): p. 1016-1024.
44. Holth, J. K., et al., The sleep-wake cycle regulates brain interstitial fluid tau in mice and CSF tau in humans. Science, 2019. 363(6429): p. 880-884.

SUMMARY

Technical Problem

It is a commonly established theory that the cerebral vasculatures become stiff/hardened according to aging, and decreases artery pulsation facilitating the circulation of the brain lymphatic system. This translates to increased likelihood of Alzheimer's disease. Furthermore, sleep clears waste products from the brain by increasing the function of the brain lymphatic system. Therefore, artificial means of activating lymphatic function/clearance will improve a variety of problems in association with sleep deprivation. Therefore, how to clear lymphatic wastes of the brain rapidly and efficiently have been the subjects of investigation.

Currently, methods are severely limited in increasing the region-specific lymphatic clearance. Ultrasound has been applied to the brain with concomitant intravenous injection of microbubble-based ultrasound contrast agents. This technique disturbs and temporarily opens the BBB by pushing endothelial cells of surrounding cerebral vessels out via amplification of the localized ultrasound pressure due to inertial-/stable-cavitation of the injected microbubble contrast agents. This technique was originally developed to deliver therapeutic drugs (having a large molecular weight) across the BBB. Despite this original intention, recent studies have suggested that the plasma/CSF/ISF which leak through the disrupted BBB may also allow for facilitating the brain lymphatic function. However, the technique suffers from serious drawbacks of potentially causing cerebral hemorrhage (critical risk factor) if the BBB is excessively disturbed or destroyed, which causes the blood cells to be leaked out of the cerebral vasculature. Furthermore, the technique cannot be used among the individuals who are allergic to or counter-indicated to the use of microbubble contrast agents.

The present disclosure is provided to solve conventional problems as described above. The object of the present disclosure is to describe an ultrasound device for facilitating waste clearance of the brain lymphatic system by applying dynamic ultrasound pressure waves passing through the skull of mammals to the deep brain areas, which enhances bulk flow movement of solutes included in brain wastes so as to increase absorption thereof into paravascular spaces.

The net effects is an increase the lymphatic drainage of the CNS. The present disclosure does not require the injection of microbubble contrast agents.

Meanwhile, technical objects to be achieved in the present disclosure are not limited to the aforementioned technical objects, and other technical objects, which are not mentioned above, will be apparently understood to a person having ordinary skill in the art from the following description.

Technical Solution

According to a first aspect of the present disclosure, an ultrasound device for facilitating waste clearance of the brain lymphatic system may include: a first frequency-generator 210 generating a predetermined frequency; a first waveform modulator 230 modulating a waveform of the frequency; a first linear amplifier 250 amplifying the waveform; a first resonance circuit portion 170a matching impedance of the ultrasound transducer 100; and a first ultrasound transducer 100 coupled to the first resonance circuit portion 170a and irradiating ultrasound 30 toward deep brain areas 10 of mammals, wherein the ultrasound 30 facilitates clearance of lymphatic wastes of the brain 10.

According to another aspect of the present disclosure, optionally, the ultrasound device for facilitating waste clearance of the brain lymphatic system may further include: a second frequency-generator 310 generating a predetermined frequency; a second waveform modulator 330 modulating a waveform of the frequency; a second linear amplifier 350 amplifying the waveform; a second resonance circuit portion 170b matching impedance of the amplified waveform; and a second ultrasound transducer 200 coupled to the second resonance circuit portion 170b and irradiating ultrasound 30 toward a deep brain areas 10 of the mammals, wherein the first ultrasound transducer 100 and the second ultrasound transducer 200 are disposed in a circumference of the brain 10 to face toward the deep part of the brain, including, but not limited to the structures such as the hippocampus or the thalamus.

According to another aspect of the present disclosure, the ultrasound device for facilitating waste clearance of the brain lymphatic system may further include: a head gear 20 to which the first ultrasound transducer 100 and the second ultrasound transducer 200 are attached.

According to another aspect of the present disclosure, the first ultrasound transducer 100 and the second ultrasound transducer 200 may be positioned so as to apply ultrasound 30 toward a deep brain area of the brain 10 from both hemispheres of the head.

According to another aspect of the present disclosure, the first ultrasound transducer 100 and the second ultrasound transducer 200 may apply ultrasound 30 simultaneously or sequentially in time-interleaved fashion.

According to another aspect of the present disclosure, the first ultrasound transducer 100 may further include a coupling gel 40 on its surface so as to acoustically couple the ultrasound to skin of the mammals.

According to another aspect of the present disclosure, the ultrasound 30 may operate in a band of 100 KHz to 500 KHz.

According to another aspect of the present disclosure, an intensity of the ultrasound 30 may be a spatial peak pulse average intensity ($I_{sppa}$) ranging from 0.1 to 190 Watt/cm².

According to another aspect of the present disclosure, a focal point of the ultrasound 30 may be a spatial peak temporal average intensity ($I_{sppa}$) ranging from 100 to 720 mWatt/cm².

According to another aspect of the present disclosure, a tone burst duration (D) of the ultrasound 30 may range from 100 ms to 500 ms.

According to another aspect of the present disclosure, the ultrasound 30 irradiated for more than 10 minutes.

Advantageous Effects

According to one embodiment of the present disclosure, an ultrasound device is capable of facilitating waste clearance of the brain lymphatic system such as β-amyloid protein and tau protein by irradiating ultrasound to the deep brain areas of mammals through the skull, then inducing bulk flow by dynamic pressure, whereby enhancing the movement of solutes in brain wastes to induce absorption thereof into the paravascular spaces.

Further, according to the present disclosure, the ultrasound device is capable of irradiating ultrasound to different areas of the brain (e.g.: left brain and right brain) sequentially or simultaneously.

Further, according to the present disclosure, the ultrasound device does not use the microbubble contrast-agents to enhance the brain lymphatic drainage, whereby preventing the occurrence of the deleterious effects of the microbubble (allergic reactions and cerebral hemorrhage increases, i.e., risks according to BBB disturbance).

Meanwhile, advantageous effects to be obtained in the present disclosure are not limited to the aforementioned effects, and other effects, which are not mentioned above, will be apparently understood to a person having ordinary skill in the art from the following description.

BRIEF DESCRIPTION OF THE DRAWINGS

The accompanying drawings of this specification exemplify a preferred embodiment of the present disclosure, the spirit of the present disclosure will be more clearly understood from the following detailed description taken in conjunction with the accompanying drawings, and thus it will be understood that the present disclosure is not limited to only contents illustrated in the accompanying drawings.

DETAILED DESCRIPTION

Description of Embodiments

Figure 1:
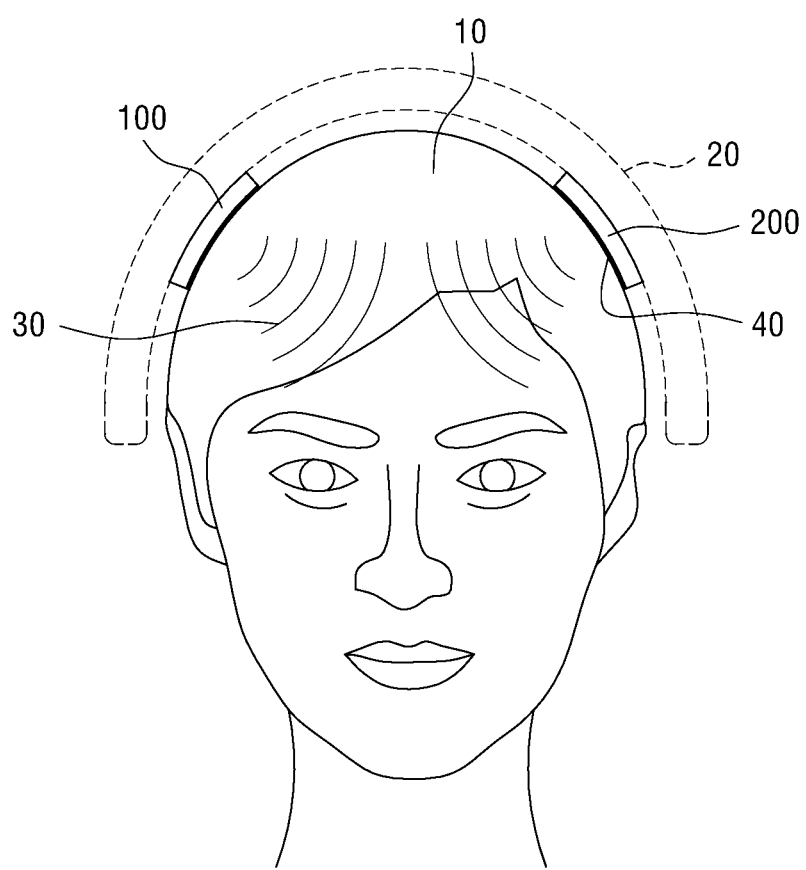
FIG. 1 is a first example for wearing an ultrasound device according to the present disclosure.

Hereinafter, embodiments of the present disclosure will be explained in detail with reference to the accompanying drawings in order to be easily implemented by those having ordinary knowledge in the art to which the present disclosure pertains. However, the following detailed description merely delineates the embodiments for structural or functional explanation of the present disclosure. Thus, it should be not interpreted that the scope of the present disclosure is limited to the embodiments explained in the specification. That is, since the embodiments are able to be modified variously and have a variety of forms, it should be understood that the scope of the present disclosure include equivalents capable of implementing the technical idea. Further, the objects or effects provided in the present disclosure do not mean that a particular embodiment includes either all of them or such effects only. Thus, it should be not understood that the scope of the present disclosure is limited thereto.

The terms used in the present disclosure should be understood as the followings.

Since the terms, such as "first", "second", etc., are used for distinguish one element from other elements, the scope of the present disclosure should be not limited thereto. For example, "a first element' may be referred to as "a second element" and similarly hereto, "a second element" may be referred to as "a first element". When mentioning that an element is "connected" to the other element, it may be connected directly thereto, however, it should be understood that there may be another element between them. Whereas, when mentioning that an element is "connected directly" to the other element, it should be understood that there may be not any other element between them. Meanwhile, it should be also understood in the same way as the above in case of expressions for explaining the relationship between elements, i.e. "between~" and "directly between~", or "adjacent to~" and "adjacent directly to~".

It should be understood that the singular expression includes the plural expression unless specifically stated otherwise. The terms, such as "comprise" and "have", etc., indicate the existences of the implemented features, numbers, steps, operations, elements, components or any of combinations thereof. It should be understood that they do not preclude the potential existences or additions of one or more features, numbers, steps, operations, elements, components or any of combinations thereof.

Unless otherwise defined, all terms used herein have the same meanings as those commonly understood by those having ordinary knowledge in the art to which the present disclosure pertains. It should be understood that the terms defined in commonly used dictionaries, should be interpreted to be consistent with the meanings contextually stated in the field of relevant art and will not be interpreted to have idealized or excessively formalistic senses unless explicitly defined in the present disclosure.

Configuration of a First Embodiment

Figure 3:
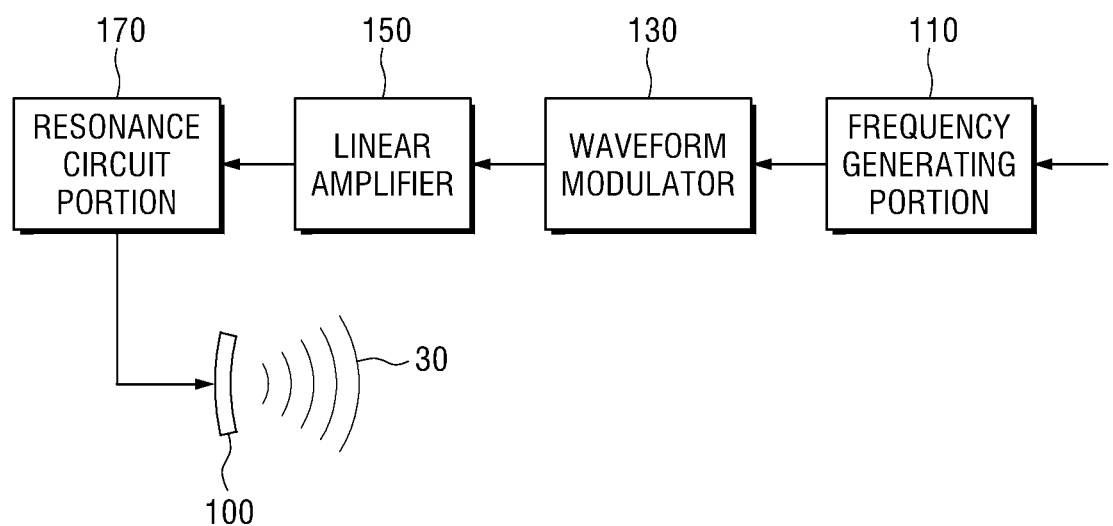
FIG. 3 is an exemplary block diagram of an ultrasound device for facilitating waste clearance of the brain lymphatic system according to the present disclosure.

Hereinafter, a configuration of a preferable embodiment will be described referring to accompanying drawings. In a first embodiment of the present disclosure, disclosed is a configuration for operating a first ultrasound transducer 100 only. FIG. 3 is an exemplary block diagram of an ultrasound device for facilitating waste clearance of the brain lymphatic system according to the first embodiment of the present disclosure. As shown in FIG. 3, a frequency-generator 110 generates a predetermined low frequency (e.g.: sinusoidal waveform in a band of 100 KHz to 500 KHz). Ultrasound by a frequency exceeding 500 KHz is absorbed in the human skull to the extent of approximately 70% or more, thus lowering efficiencies thereof. As taking a transmittance of the skull into account, a band of 100 KHz to 200 KHz is more preferable. For reference, the ultrasound used in the ultrasound imaging is a high frequency in a band of 1 MHz to 15 MHz.

Further, in one embodiment of the present disclosure, an intensity of the ultrasound 30 is a spatial peak pulse average intensity ($I_{sppa}$) ranging from 0.1 to 190 Watt/cm$^2$.

Further, in one embodiment of the present disclosure, an intensity of the ultrasound 30 is a spatial peak pulse average intensity ($I_{sppa}$) ranging from 0.1 to 190 Watt/cm$^2$. Internationally permissible intensity for humans is 190 Watt/cm$^2$ at the maximum which is applied to medical ultrasound imaging systems.

Further, a focal point of the ultrasound 30 has a spatial peak temporal average intensity ($I_{spta}$) ranging from 100 to 720 mWatt/cm$^2$. Internationally-permissible limit for humans is 720 mW/cm$^2$ at the maximum, which is applied to medical ultrasound imaging systems.

Further, a tone burst duration (D) of the ultrasound 30 ranges from 100 ms to 500 ms, operating at a duty cycles to an extent from 0.3 to 50%. If D is lower than 100 ms, a clearance facilitation effect is less significant. If exceeding 500 ms, a duty cycle is adjusted (i.e. reduced) not to exceed $I_{spta}$ depending on relevant $I_{sppa}$. Excessive $I_{spta}$, in general, may elevate the temperature of tissues, and thus should be avoided.

A waveform modulator 130 modifies a waveform of a generated frequency into waveform having a pulse envelope 60 or a half sine envelop 65.

A linear amplifier 150 amplifies the modified pulse waveform to a predetermined extent.

A resonance circuit portion 170 matches an impedance of the ultrasound transducer.

The first ultrasound transducer 100 is coupled to the resonance circuit portion 170, irradiating ultrasound. Further, the first ultrasound transducer 100 is capable of being fixed to a head gear 20, thus being fixed to a wearer as the individual wears the head gear 20. The first transducer 100 is aligned so as to irradiate the ultrasound 30 of dynamic pressure wave with a wide focal area to a direction of deep areas of the brain 10 (e.g., the hippocampus).

The first ultrasound transducer 100 is constituted with a plurality of ultrasound probe arrays or a single-element piezo-material and has a structure adopted to generate a low-intensity ultrasound. The ultrasound probe array of the first ultrasound transducer 100 has a structure that (1) a plurality of ultrasound elements that are arranged coaxially in a circular or asymmetrical form, or (2) a plurality of disc-typed (circle or square) ultrasound elements is arranged toward a specific direction. (3) A single-element piezo-material can also be adopted. The plurality of ultrasound probes of the first transducer 100 regulates each phase, thus being endowed with a function to focus ultrasound into a specific position and also regulates the phases, thus regulating ultrasound directions (beam steering). In case of a single-element transducer, the geometry and direction of the transducer determines the position of the beam focus and the direction of the ultrasound. The transducer may have either focused or non-focused configuration, depending on the area of sonication.

In the first embodiment of the present disclosure, the configuration is made up of the first ultrasound transducer 100 only. The first ultrasound transducer 100 works independently but not requiring the focusing ability to an extent of traditionally-defined focused ultrasound. On the other hand, in order to maximize dynamic pressure effects, ultrasound in a low frequency band is used.

The ultrasound 30 irradiated by the first ultrasonic transducer 100 pushes solutes including various wastes, from the exterior of the brain to the deep areas thereof, to the deep brain areas. In such a process, bulk flow of ISF is induced by the dynamic pressure of the ultrasound, thus enhancing the movement of solutes including brain wastes. Whereby, the solutes are absorbed more rapidly in the paravascular space, thus allowing for facilitated clearance of lymphatic wastes of the brain.

And, a coupling gel 40 is applied between the first ultrasonic transducer 100 and wearer's scalp, thus configuring a coupling acoustically. The coupling gel 40 is made from synthetic materials capable of elastic compression so as to allow the coupling gel 40 to adhere closely to a curve of the scalp, and this may include hydrous gel or silicone such as Poly-vinyl Alcohol (PVA) from which gas is removed.

Figure 5:
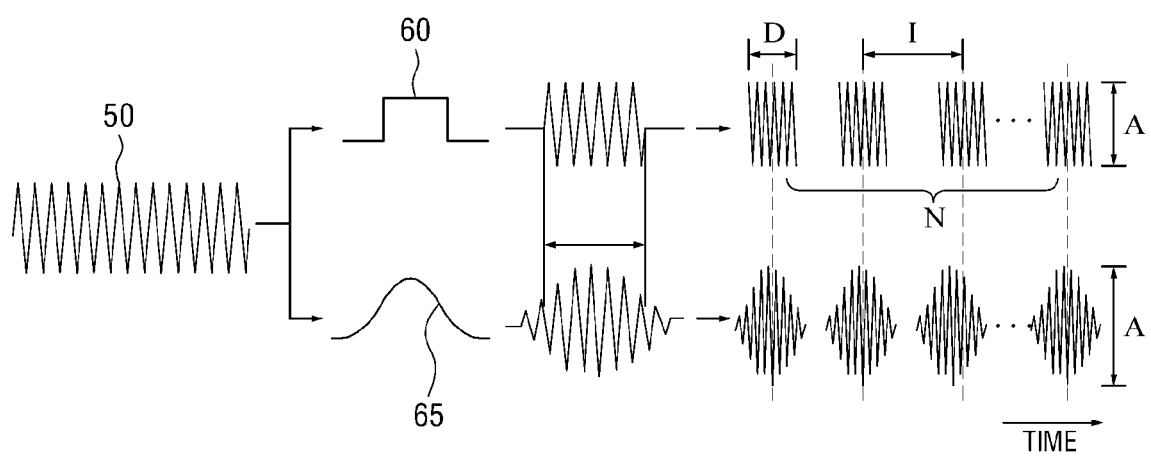
FIG. 5 is a diagram of a waveform showing modification in a waveform of ultrasound used in an ultrasound device according to the present disclosure.

FIG. 5 is a diagram of a waveform showing modification in a waveform of the ultrasound 30 used in the ultrasound device according to the present disclosure. As shown in FIG. 5, frequency 50 generated in the frequency-generator 110 may be modified by using the pulse envelope 60 or the half sine envelope 65. At this time, D, as the Tone Burst Duration (TBD), ranges 100 ms to 500 ms. 'I' means Inter-Pulse-Interval (IPI; expressed in second). The inverse number of I is, as Pulse Repetition Frequency (PRF), expressed as Hertz. TBD and PRF together determine a duty cycle (%) that is a ratio of a period (i.e., time it takes for irradiating ultrasound) occupied by TBD×PRF per second. The number (N) of pulses is controlled, then determining total time it takes for irradiating the ultrasound, and intensity/power of the ultrasound is determined by adjusting the magnitude (A) of peak-to-peak of the waveform.

Configuration of a Second Embodiment

Hereinafter, a configuration of a second embodiment will be described referring to accompanying drawings. In the second embodiment of the present disclosure, the disclosed are configurations for operating a first ultrasound transducer 100 and a second ultrasound transducer 200.

Figure 4:
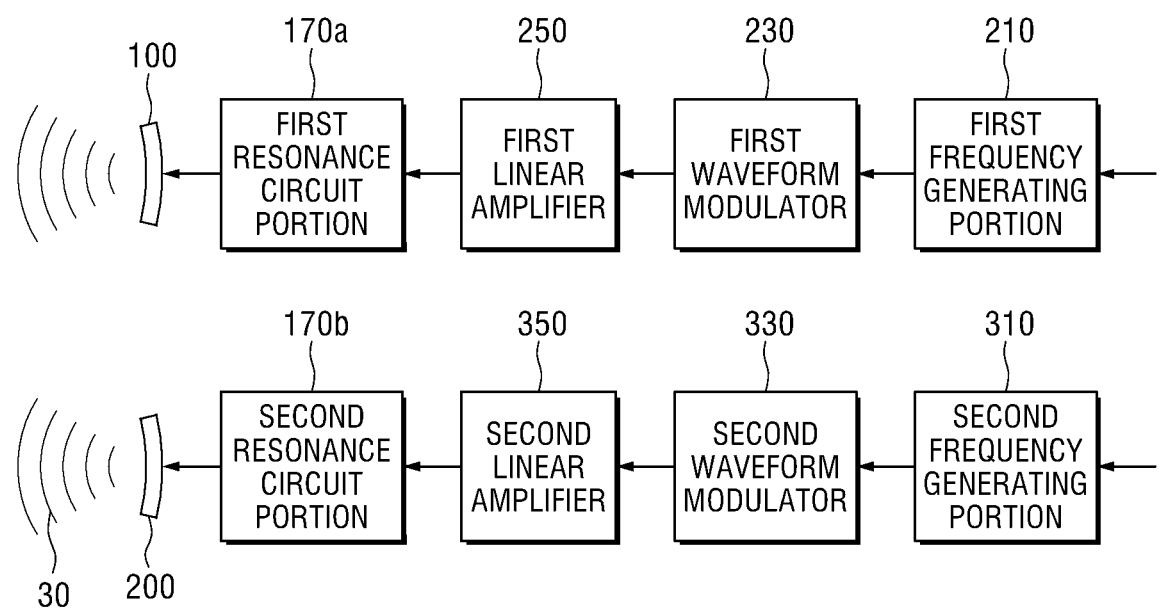
FIG. 4 is an exemplary block diagram of an ultrasound device for facilitating waste clearance of the brain lymphatic system according to a second embodiment of the present disclosure.

FIG. 4 is an exemplary block diagram of an ultrasound device for facilitating waste clearance of the brain lymphatic system according to the second embodiment of the present disclosure. As shown in FIG. 4, in order to operate the first ultrasonic transducer 100, the ultrasound device has a first frequency-generator 210, a first waveform modulator 230 and a first linear amplifier 250. And, in order to operate the second ultrasonic transducer 200, the ultrasound device has a second frequency-generator 310, a second waveform modulator 330 and a second linear amplifier 350. The first frequency-generator 210 and the second frequency-generator 310 are the same as the frequency-generator 110 according to the first embodiment in configurations and functions. The first waveform modulator 230 and the second waveform modulator 330 are the same as the waveform modulator 130 according to the first embodiment in configurations and functions. The first linear amplifier 250 and the second linear amplifier 350 are the same as the linear amplifier 150 according to the first embodiment in configurations and functions. A first resonance circuit portion 170a and a second resonance circuit portion 170b are the same as the resonance circuit portion 170 according to the first embodiment in configurations and functions. The first ultrasound transducer 100 and the second ultrasound transducer 200 are identical with each other in configurations and functions but may be different in installation positions and irradiated frequencies, as necessary.

Further, in configurations of the second embodiment, configurational elements having a plurality channels may be merge with each other. For example, the first and second linear amplifiers 250, 350 may be replaced with one linear amplifier having outputs for a 2-channel amplifier. Further, the first and second frequency-generators 210, 310 may be replaced by dividing a frequency output from one frequency-generator.

FIG. 1 is a first example for wearing the ultrasound device according to the present disclosure. As shown in FIG. 1, the first and second ultrasound transducers 100, 200 are installed in the head gear 20, and are positioned closely to the scalp as a wearer wears the head gear 20. Particularly, in the first example, the first and second ultrasound transducers 100, 200 are positioned in the vicinity of opposite temples of the wearer respectively, then being aligned so as to irradiate the ultrasound (30) toward the deep areas of the brain 10.

Figure 2:
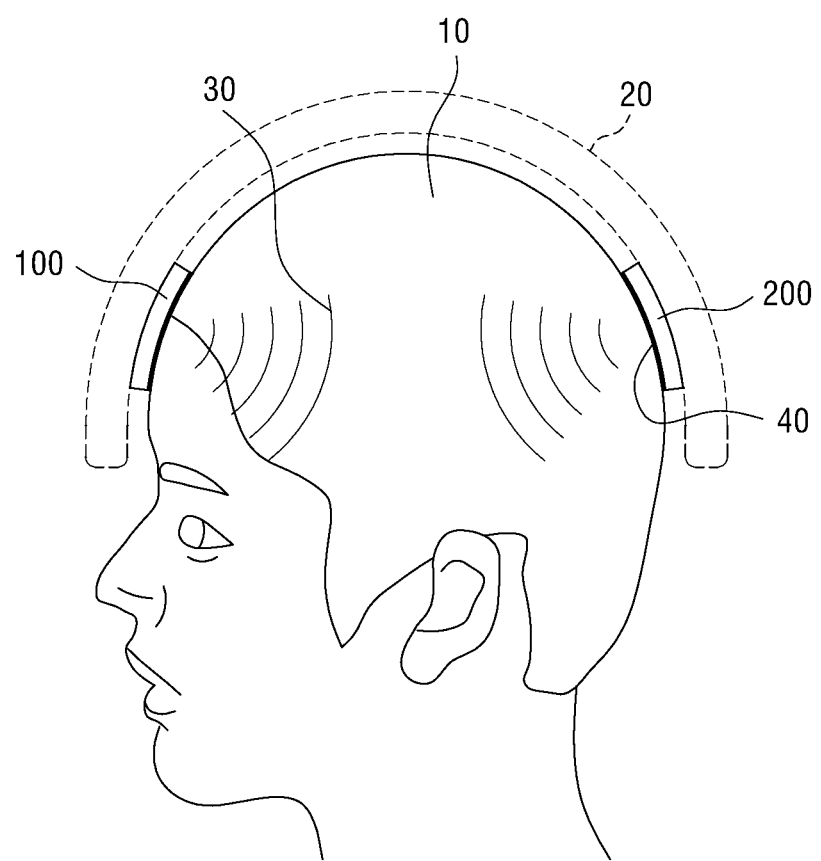
FIG. 2 is a second example for wearing an ultrasound device according to a first embodiment of the present disclosure.

FIG. 2 is a second example for wearing the ultrasound device according to a first embodiment of the present disclosure. As shown in FIG. 2, the first ultrasound transducer 100 adheres closely to a forehead region of the wearer and the second ultrasound transducer 200 is aligned so as to adhere closely to a region of the back of wearer's head. It is the same to align the first and second transducers so as to irradiate the ultrasound 30 toward the deep areas of the brain 10 as in the aforementioned first example.

Figure 6:
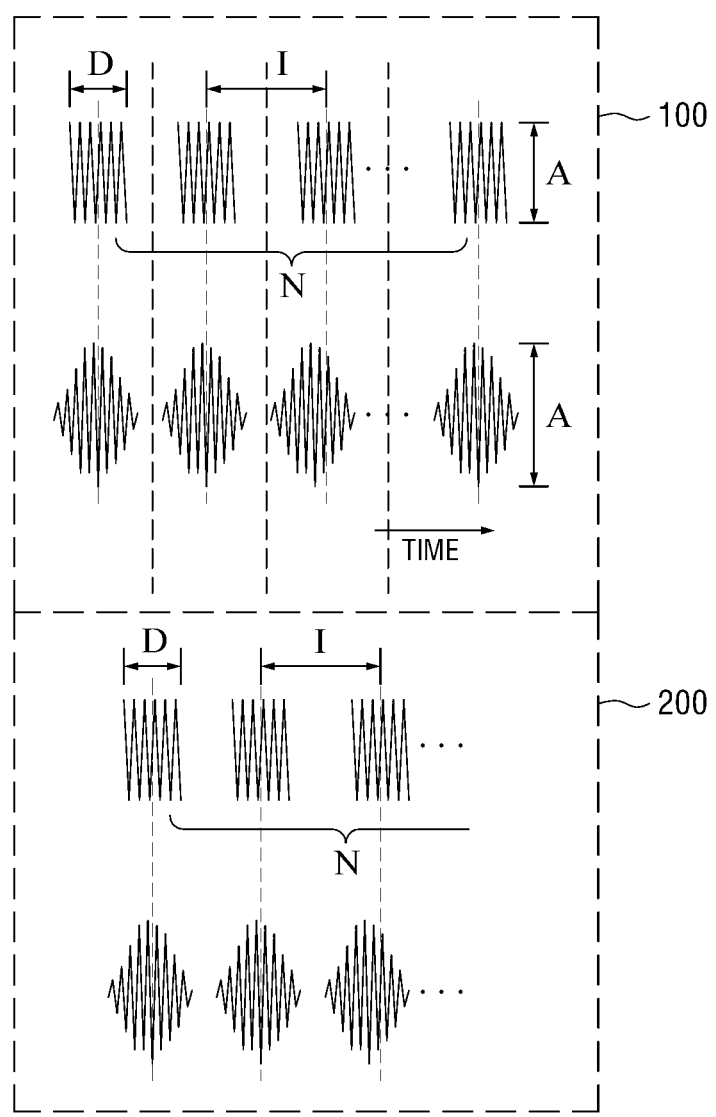
FIG. 6 is a diagram of a waveform when first and second ultrasound transducers work sequentially in time-interleaved fashion for the second embodiment of the present disclosure.

FIG. 6 is a diagram of a waveform when the first and second ultrasound transducers 100, 200 work sequentially in time-domain according to the second embodiment of the present disclosure. The first and second ultrasound transducers 100, 200 may work at the same time, and also work sequentially as shown in FIG. 6. That is, the second ultrasonic transducer 200 irradiates the ultrasound 30 at intervals of the first ultrasound transducer 100 irradiates the ultrasound 30. At this time, the waveform and frequency of the first ultrasound transducer 100 may be the same as and also differ from the waveform and frequency of the second 200.

Operations of Embodiments

Hereinafter, an operation of the first embodiment will be described in detail referring to accompanying drawings. Firstly, the coupling gel 40 is applied to the first ultrasound transducer 100 and the wearer's scalp, respectively. The head gear 20 is then put on the wearer's head, so as that the first ultrasound transducer 100 is applied over the scalp. Common ultrasound gel is applied to all surface interfaces to promote acoustic coupling.

A constant frequency 50 is generated by power supply applied to the frequency-generator 110, then being modulated into a form of pulse wave or half sine wave by waveform modulator 130, followed by being amplified to a predetermined output by the linear amplifier 150 and matched with impedance by the resonance circuit portion 170. The ultrasound 30 is then irradiated from the first ultrasound transducer 100.

The irradiated ultrasound 30 passes the skull and then passes through the brain, thus being toward the deep brain areas. In such a process, bulk flow of ISF is induced by the dynamic pressure of the ultrasound, thus enhancing the movement of solutes including brain wastes. Whereby, the solutes are absorbed more rapidly in the paravascular space, thus allowing facilitating clearance of lymphatic wastes of the brain.

Total irradiation time of the ultrasound 30 may approximate 30 to 40 minutes. This is because if the irradiation time becomes longer, the wearer may feel uncomfortable while the coupling gel 40 starts to dry at a room temperature, reducing the acoustic efficiency.

Further, the ultrasound may be irradiated to multiple regions of the brain sequentially or simultaneously.

Modification Example

According to a modification example of the present disclosure, 3 or more ultrasound transducers may be provided and disposed to be dispersed around the head of mammals.

Further, in order to optionally enhance the circulation in a specific region of the brain, it is allowable to use one or more focused ultrasound transducers instead of non-focal ones.

Melamine Foam Model Experiment

Figure 7A:
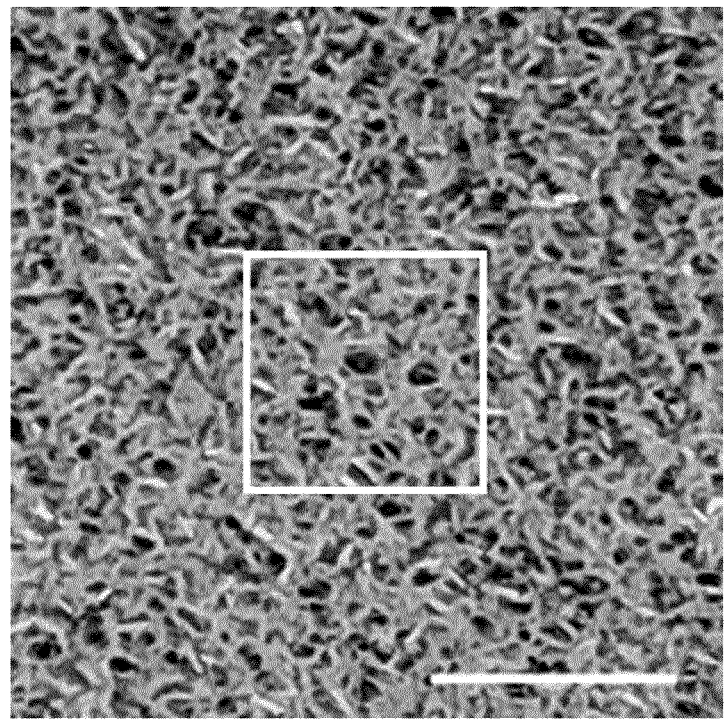
FIG. 7A is a microscopic photograph of a melamine foam used in melamine foam modeling according to the present disclosure (bar=1 mm)
Figure 7B:
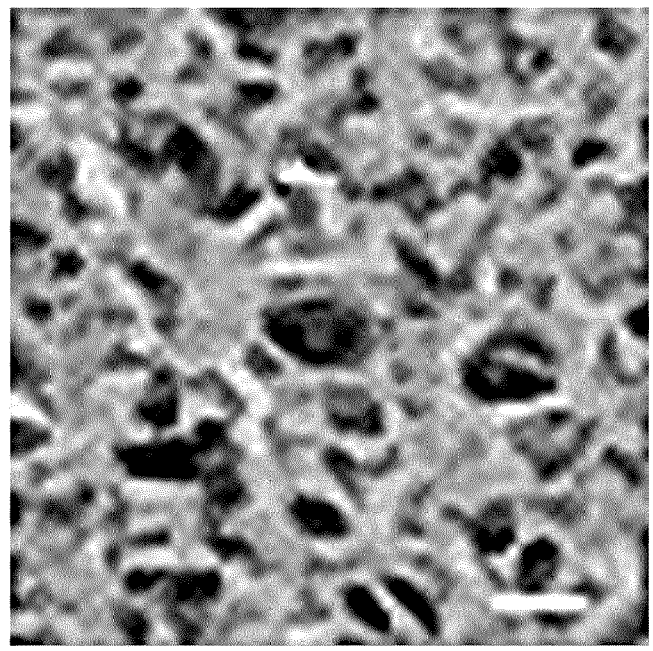
FIG. 7B is an enlarged photograph of an area region in FIG. 7A (bar=100 μm)

Hereinafter, a modeling experiment will be described in order to verify effects of the present disclosure. Firstly, FIG. 7A is a microscopic photograph of a melamine foam used in the modeling according to the present disclosure, and FIG. 7B is an enlarged photograph of its area region in FIG. 7A. To physically model the paravascular space of the brain, an object material should be (1) densely occupied, (2) hydrophilic, having (3) small micro-sized pores within. Chemical features of a melamine foam 420 are not 'identical' to tissue materials constituting the paravascular space of the brain. Notwithstanding, the melamine foam 420 is an appropriate inorganic material for testing the validity of the present disclosure on the basis of a fact that this is a multi-porous hydrophilic material having pore sizes ranging from 5 to ~50 μm. The leptomeningeal vasculature in the paravascular space in humans has multi-porous stomata having a pore size of approximately 5 μm.

Figure 8:
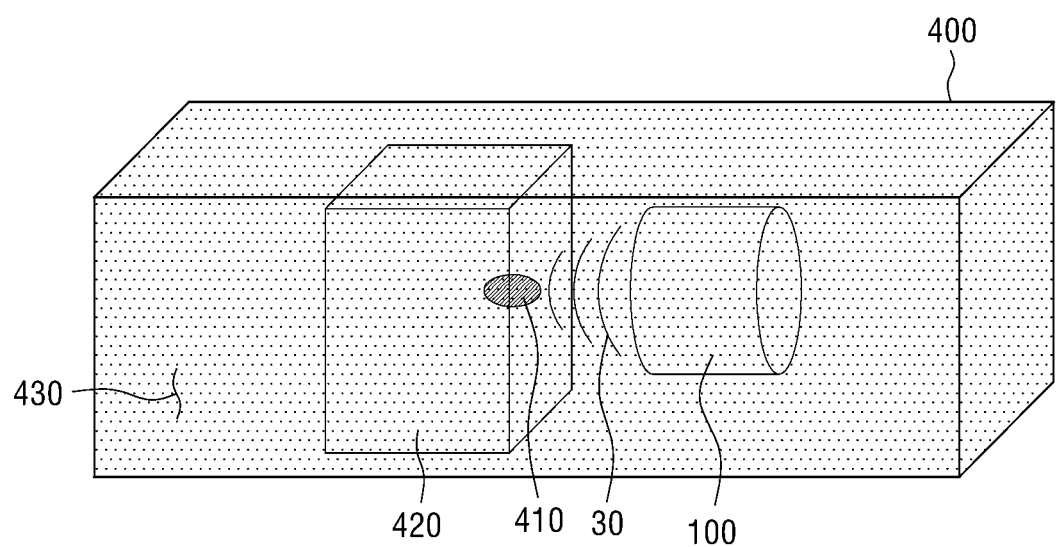
FIG. 8 is an exemplary block diagram illustrating a configuration of a modeling experiment according to the present disclosure.

FIG. 8 is an exemplary block diagram illustrating a configuration of a modeling experimental setup according to the present disclosure. As shown in FIG. 8, in order to model cerebrospinal fluid (CSF) and impurities (wastes) included therein, 2.3 g of a food dye (Brilliant Blue FCF, molecular weight of 792.85 g/mol) was dissolved in 4.6 L of distilled water (not degassed). The molecular weight of the food dye (Brilliant Blue FCF) 410 corresponds to the solutes of the brain and also corresponds to macromolecular solutes which cannot pass through the blood-brain-barrier (BBB). The melamine foam 420 was first immersed in dye-free distilled water, allowing the water to be absorbed into the pores. This procedure modeled the paravascular space containing the CSF. Then, as shown in FIG. 8, melamine foam 420 was transferred to the tank 400 containing distilled water with a Brilliant Blue FCF 430. A focused ultrasound transducer 100, operating in 500 kHz frequency, was immersed in dye-containing water 430. The focus of the acoustic pressure wave was aimed to sonicate the surface of the melamine foam.

Figure 9A:
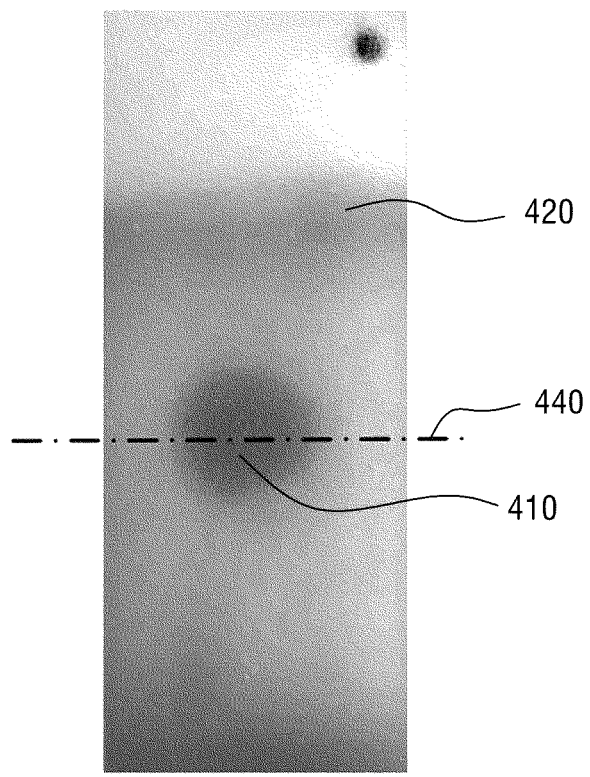
FIG. 9A is a photograph of a state that a food dye (Brilliant Blue FCF) 410 infiltrates into the melamine foam 420.
Figure 9B:
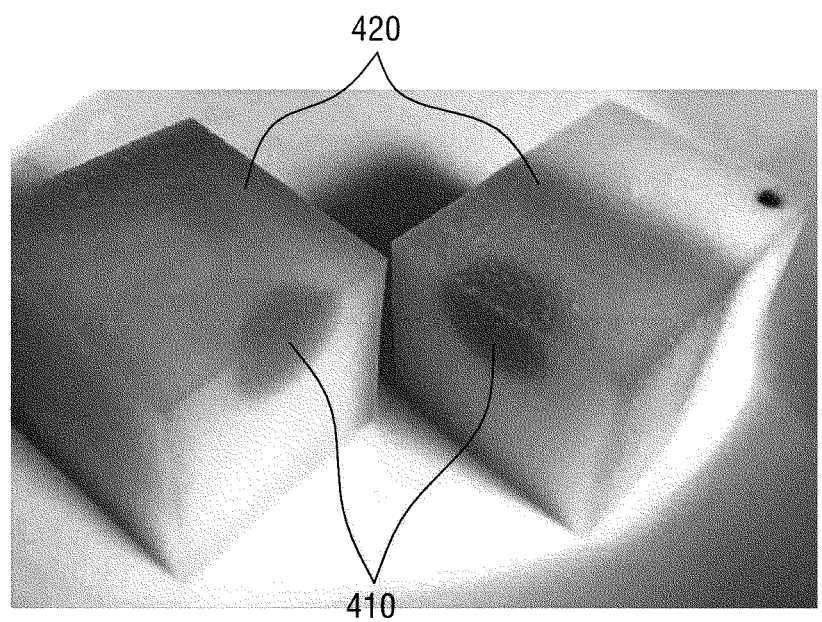
FIG. 9B is a photograph of the melamine foam cut along the surface 440 in FIG. 9A.

As time goes by, the dye 410 infiltrates into the melamine foam 420 through diffusion, whereby a convective bulk flow that incurred by the application of ultrasound 30 helped deeper infiltration of the dye 410 in an area where the ultrasound 30 is applied to the surface of the foam. FIG. 9A is a photograph of a state that dyes 410 infiltrate into the melamine foam 420, and FIG. 9B is a photograph of the melamine foam cut along the surface 440 in FIG. 9A.

After the experiment, following cutting along a cut surface 440, quantification was made by measuring an infiltration depth of the dyes 410 repeatedly 10 times. Tested were experimental conditions of 8 kinds of different combinations of ultrasound parameters and a control condition (without applying any ultrasound). The experimental conditions and measurement results are as shown in [Table 1].

TABLE 1

| Condition | TBD(ms) | Duty cycle (%) | $I_{sppa}$ (Watt/cm$^2$) | Infiltration distance (mean ± std in mm; n = 10) |
|---|---|---|---|---|
| Ultrasound | 200 | 40 | 2 | 11.1 ± 1.8* |
| | | | 1 | 1.5 ± 0.4 |
| | | 20 | 2 | 6.7 ± 0.4* |
| | | | 1 | 0.9 ± 0.2 |
| | 0.2 | 40 | 2 | 2.6 ± 0.5* |
| | | | 1 | 1.0 ± 0.2 |
| | | 20 | 2 | 1.5 ± 0.6 |
| | | | 1 | 0.7 ± 0.2 |
| Comparison control group (not using ultrasound) | Not applicable | Not applicable | Not applicable | 1.1 ± 0.3 |

*has a significant difference, p < 0.05, as compared with the comparison control group (one-tailed t-test).

The results indicate that depth of infiltration through passive diffusion of the dye into the foam reached about 1.1 mm distance from the surface (without application of the ultrasound) while about 10-fold increase in dye penetration (i.e., 11 mm penetration) was achieved by applying ultrasound given at 200 ms of TBD with 40% duty cycle. Through this modeling experiment, it was verified that the ultrasound induces the Brilliant Blue FCF dyes to infiltrate into the melamine foam by the bulk flow more than the diffusion.

In addition, even though being under the same condition of 40% of a duty cycle and 2 Watt/cm$^2$ of an intensity, it was verified that 200 ms of TBD showed an increased infiltration approximately 4 folds or more, compared to the use of 0.2 ms of TBD. This also verifies that it is more efficient to use 200 ms or more of TBD at an identical intensity, i.e., identical $I_{spta}$ (identical duty cycle condition) than the use of shorter TBD, all in order to create bulk motion of the solutes. Dynamic bulk flow induced by a longer TBD is greater than a flow created by the use of a shorter TBD, thus being more advantageous in moving the solutes (i.e. dyes).

As mentioned above, the detailed description for the disclosed preferable embodiments of the present disclosure was provided in order to be easily implemented by those skilled in the art. In the above, the preferable embodiments of the present disclosure were explained with reference to the accompanying drawings, it will apparent for those skilled in the art that various changes and modification are allowable within the scope of the present disclosure. For example, those skilled in the art are able to use the respective configurations described in the aforementioned embodiments in a way of combining the same with each other. Thus, the present disclosure is not limited to the embodiments shown in this application, but granting the widest scope coinciding with principals and novel features disclosed herein.

The present disclosure may be rectified to different specific forms within the scope of the spirit and essential features. Thus, the above detailed description should not be understood limitedly in all aspects but should be considered as examples. The scope of the present disclosure should be determined by interpreting accompanying claims rationally, and includes all modifications within the equivalent scope of the present disclosure. The present disclosure is not limited to the embodiments shown in this application, but granting the widest scope coinciding with principals and novel features disclosed herein. Further, the present disclosure may configure embodiments by combining claims which are not in explicit citation relationship in the patent scope or may include new claims through amendments following filing this application.

FIGURE REFERENCE NUMBERS

10: brain
20: head gear,
30: ultrasound
40: coupling gel (gel),
50: electrical waves with a frequency
60: pulse envelope,
65: half-sine envelope,
100: first ultrasound transducer,
110: frequency-generator,
130: waveform modulator,
150: linear amplifier,
170: resonance circuit portion,
170a: first resonance circuit portion,
170b: second resonance circuit portion,
200: second ultrasound transducer,
210: first frequency-generator,
230: first waveform modulator,
250: first linear amplifier,
310: second frequency-generator,
330: second waveform modulator,
350: second linear amplifier,
400: tank,
410: food dye,
420: melamine foam,
430: dye-dissolved water,
440: cut surface,
D: Tone Burst Duration (TBD),
I: Inter-Pulse-Interval (IPI),
N: number of pulse,
A: peak-to-peak size of waveform,
$I_{sppa}$: space-peak pulse-average intensity,
$I_{spta}$: space-peak time-average intensity.

The invention claimed is:

1. An ultrasound device configured to facilitate lymphatic waste clearance of a brain lymphatic system, the ultrasound device comprising:

a first frequency-generator configured to generate a first frequency that is of an ultrasound waveform in a band of 100 KHz to less than 200 KHz;
a first waveform modulator configured to modulate the ultrasound waveform of the first frequency;
a first linear amplifier configured to amplify the ultrasound waveform of the first frequency;
a first resonance circuit portion configured to match impedance of the amplified ultrasound waveform of the first frequency;
a first ultrasound transducer coupled to the first resonance circuit portion and configured to irradiate the amplified ultrasound waveform of the first frequency toward a brain of a mammal to facilitate the lymphatic waste clearance of the brain lymphatic system;
a second frequency-generator configured to generate a second frequency that is of an ultrasound waveform in a band of 100 KHz to less than 200 KHz;
a second waveform modulator configured to modulate the ultrasound waveform of the second frequency;
a second linear amplifier configured to amplify the ultrasound waveform of the second frequency;
a second resonance circuit portion configured to match impedance of the amplified ultrasound waveform of the second frequency; and
a second ultrasound transducer coupled to the second resonance circuit portion and configured to irradiate the amplified ultrasound waveform of the second frequency toward the brain of the mammal to facilitate the lymphatic waste clearance of the brain lymphatic system,
wherein the first ultrasound transducer and the second ultrasound transducer are configured to be disposed in a circumference of the brain facing toward a deep area of the brain,
wherein a tone burst duration (D) of the amplified ultrasound waveforms of the first and second frequencies ranges from 100 ms to 500 ms, and
wherein the amplified ultrasound waveforms of the first and second frequencies facilitate the lymphatic waste clearance of the brain.

2. The ultrasound device according to claim 1, further comprising:
a head gear to which the first ultrasound transducer and the second ultrasound transducer are fixed.

3. The ultrasound device according to claim 1, wherein the first ultrasound transducer and the second ultrasound transducer are aligned so as to irradiate the amplified ultrasound waveforms of the first and second frequencies toward the deep brain area.

4. The ultrasound device according to claim 1, wherein the first ultrasound transducer and the second ultrasound transducer irradiate the amplified ultrasound waveforms of the first and second frequencies sequentially or simultaneously.

5. The ultrasound device according to claim 1, wherein the first ultrasound transducer comprises a coupling gel so as to be acoustically coupled to a skin of the mammal.

6. The ultrasound device according to claim 1, wherein an intensity of the amplified ultrasound waveforms of the first and second frequencies is a spatial peak pulse average intensity ($I_{sppa}$) ranging from 0.1 to 190 Watt/cm$^2$.

7. The ultrasound device according to claim 1, wherein a focal point of the amplified ultrasound waveforms of the first and second frequencies is a spatial peak temporal average intensity ($I_{spta}$) ranging from 100 to 720 mWatt/cm$^2$.

* * * * *